United States Patent
Nair et al.

(10) Patent No.: US 9,469,589 B2
(45) Date of Patent: Oct. 18, 2016

(54) PROCESS FOR PRODUCING PHENOL AND/OR CYCLOHEXANONE

(71) Applicant: ExxonMobile Chemical Patents Inc., Baytown, TX (US)

(72) Inventors: Hari Nair, Somerville, NJ (US); Christopher L. Becker, Manhattan, KS (US); Jason D. Davis, Beaumont, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/891,177

(22) PCT Filed: Jun. 4, 2014

(86) PCT No.: PCT/US2014/040828
§ 371 (c)(1),
(2) Date: Nov. 13, 2015

(87) PCT Pub. No.: WO2014/209557
PCT Pub. Date: Dec. 31, 2014

(65) Prior Publication Data
US 2016/0107970 A1    Apr. 21, 2016

Related U.S. Application Data

(60) Provisional application No. 61/841,031, filed on Jun. 28, 2013.

(30) Foreign Application Priority Data

Sep. 11, 2013  (EP) .................................... 13183954

(51) Int. Cl.
C07C 45/53   (2006.01)
C07C 37/08   (2006.01)
C07C 2/74    (2006.01)
C07C 407/00  (2006.01)

(52) U.S. Cl.
CPC ................. *C07C 45/53* (2013.01); *C07C 2/74* (2013.01); *C07C 37/08* (2013.01); *C07C 407/00* (2013.01); C07C 2101/14 (2013.01); C07C 2529/08 (2013.01)

(58) Field of Classification Search
CPC .......... C07C 45/53; C07C 37/08; C07C 2/74
USPC .................................. 568/342, 798; 585/467
See application file for complete search history.

(56) References Cited

U.S. PATENT DOCUMENTS

| | | | |
|---|---|---|---|
| 3,959,381 A | 5/1976 | Arkell et al. |
| 4,490,565 A | 12/1984 | Chang et al. |
| 5,254,751 A | 10/1993 | Zakoshansky |
| 6,037,513 A | 3/2000 | Chang et al. |

FOREIGN PATENT DOCUMENTS

| | | |
|---|---|---|
| FR | 1 088 503 | 3/1955 |
| WO | 00/14042 | 3/2000 |
| WO | 2004/009522 | 1/2004 |
| WO | 2009/131769 | 10/2009 |
| WO | 2012/134549 | 10/2012 |
| WO | 2012/145028 | 10/2012 |
| WO | 2012/145031 | 10/2012 |
| WO | 2012/145032 | 10/2012 |

*Primary Examiner* — Sikarl Witherspoon
(74) *Attorney, Agent, or Firm* — Siwen Chen; Stephen A. Baehl (57) ABSTRACT

In a process for producing phenol and/or cyclohexanone, cyclohexylbenzene is contacted with an oxygen-containing gas in the presence of an oxidation catalyst under oxidation conditions effective to produce an oxidation effluent comprising cyclohexylbenzene hydroperoxide. At least a portion of the oxidation effluent is then subjected to a concentrating step to produce a cleavage feed having a higher concentration of cyclohexylbenzene hydroperoxide than the oxidation effluent. A cleavage reaction mixture comprising the cleavage feed is then contacted with a solid acid catalyst in a cleavage reaction zone under conditions effective to produce a cleavage product comprising phenol and cyclohexanone.

22 Claims, 1 Drawing Sheet

PROCESS FOR PRODUCING PHENOL AND/OR CYCLOHEXANONE

PRIORITY CLAIM

This application is a National Stage Application of International Application No. PCT/US2014/040828 filed Jun. 4, 2014, which claims priority to U.S. Provisional Application Ser. No. 61/841,031 filed Jun. 28, 2013, and European Application No. 13183954.0 filed Sep. 11, 2013, the disclosures of which are fully incorporated herein by their reference.

CROSS REFERENCE TO RELATED APPLICATIONS

This patent application is related to U.S. Provisional Application Ser. No. 61/841,060, filed Jun. 28, 2013; U.S. Provisional Application Ser. No. 61/502,985, filed Jun. 30, 2011; U.S. application Ser. No. 14/110,266, filed Dec. 15, 2011; and U.S. application Ser. No. 14/009,827, filed Dec. 15, 2011, the disclosures of which are fully incorporated herein by their reference.

FIELD

The present disclosure relates to a process for producing phenol and/or cyclohexanone.

BACKGROUND

Phenol and cyclohexanone are important products in the chemical industry and are useful in, for example, the production of phenolic resins, bisphenol A, ε-caprolactam, adipic acid, and plasticizers.

Currently, a common route for the production of phenol is the three-step Hock process via cumene. In the first step of the process benzene is alkylated with propylene in the presence of an acidic catalyst to produce cumene. The second step comprises oxidation, preferably aerobic oxidation, of cumene to the corresponding cumene hydroperoxide. The third step comprises cleavage of the cumene hydroperoxide, usually in the presence of a sulfuric acid catalyst, into substantially equimolar amounts of phenol and acetone, a co-product.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is disclosed in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. This patent reference also discloses that the resultant cyclohexylbenzene can be oxidized to the corresponding hydroperoxide which is then decomposed to the desired phenol and cyclohexanone co-product.

The process for making phenol from cyclohexylbenzene differs from the cumene process in several respects. Firstly, oxidation of cyclohexylbenzene to cyclohexylbenzene hydroperoxide is much more difficult than oxidation of cumene and requires elevated temperatures and the use of a catalyst, such as N-hydroxyphthalimide (NHPI). As a result, the cyclohexylbenzene oxidation effluent is also generally at elevated temperatures so that cooling this stream back to ambient temperature would incur additional operating cost. Also, in view of the high boiling point of cyclohexylbenzene, concentration of the cyclohexylbenzene hydroperoxide by evaporation of the residual cyclohexylbenzene is much more difficult. In addition, the cleavage chemistry for cyclohexylbenzene hydroperoxide is much more complicated than that for cumene hydroperoxide, particularly since more routes for by-product formation exist with cyclohexylbenzene hydroperoxide. Moreover, cyclohexanone is much more prone to acid-catalyzed aldol condensation reactions than acetone so that significant yield loss is possible unless the cyclohexylbenzene hydroperoxide cleavage is closely controlled.

There are other disadvantages of using sulfuric acid for cyclohexylbenzene hydroperoxide cleavage: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

In addition, International Patent Publication No. WO2012/145031 discloses that large pore zeolites of the FAU type having a unit cell size of less than 24.50 Å exhibit a unique combination of high activity and high selectivity activity for the conversion of cyclohexylbenzene hydroperoxide into phenol and cyclohexanone.

Although a number of solid acids have shown promise as catalysts for the cleavage of cyclohexylbenzene hydroperoxide, to date their utility has been limited because of their tendency to undergo rapid deactivation. According to the present invention, it has now been found that the cycle life of solid acid catalysts used in the cleavage of cyclohexylbenzene hydroperoxide into phenol and cyclohexanone can be increased if the concentration of cyclohexylbenzene hydroperoxide in the effluent from the upstream oxidation process is increased before the effluent is supplied to the cleavage reaction.

SUMMARY

In one aspect, the present disclosure relates to a process for producing phenol, the process comprising:

(a) contacting cyclohexylbenzene with an oxygen-containing gas in the presence of an oxidation catalyst under oxidation conditions effective to produce an oxidation effluent comprising cyclohexylbenzene hydroperoxide at a first concentration Con1 and residual cyclohexylbenzene;

(b) concentrating at least a portion of the oxidation effluent to produce a cleavage feed comprising cyclohexylbenzene hydroperoxide at a second concentration Con2, where Con2>Con1; and (c) contacting a cleavage reaction mixture formed from the cleavage feed with a solid acid catalyst in a cleavage reaction zone under conditions effective to produce a cleavage product comprising phenol and cyclohexanone.

In a further aspect, the present disclosure relates to a process for producing phenol, the process comprising:

(a) hydroalkylating benzene with hydrogen in the presence of a hydroalkylation catalyst under conditions effective to produce a hydroalkylation reaction product comprising cyclohexylbenzene;

(b) contacting at least a portion of the cyclohexylbenzene from the hydroalkylation reaction product with an oxygen-containing gas in the presence of an oxidation catalyst under oxidation conditions effective to produce an oxidation effluent comprising cyclohexylbenzene hydroperoxide at a first concentration Con1 and residual cyclohexylbenzene;

(c) concentrating at least a portion of the oxidation effluent to produce a cleavage feed comprising cyclohexylbenzene hydroperoxide at a second concentration Con2, where Con2>Con1; and (d) contacting a cleavage reaction mixture formed from the cleavage feed with a solid acid catalyst in a cleavage reaction zone under conditions effective to produce a cleavage product comprising phenol and cyclohexanone.

In one embodiment, the concentrating step comprises distillation to remove at least a portion of the residual cyclohexylbenzene in the oxidation effluent such that Con2−Con1>10 wt %, or even Con2−Con1>20 wt %.

In one embodiment, Con1 is in a range from 15 to 30 wt %, such as from 20 to 25 wt %, and Con2 is in a range from 30 to 80 wt %, such as from 40 to 50 wt %.

Desirably, the cleavage product is divided into a first fraction and a second fraction, and the first fraction is recycled to the cleavage reaction zone, for example such that the weight ratio of the first fraction to the second fraction is from 1 to 50.

DETAILED DESCRIPTION OF THE EMBODIMENTS

In the present disclosure, a process may be described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement. As used herein, "wt %" means percentage by weight. As used herein, all ppm are by weight unless specified or indicated otherwise.

As used herein, the indefinite article "a" or "an" shall mean "at least one" unless specified to the contrary or the context clearly indicates otherwise. Thus, embodiments using "a solid acid" include embodiments where one, two or more type(s) of solid acids are used, unless specified to the contrary or the context clearly indicates that only one hydrogenating metal is used.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzne, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycyclohexylbenzene" shall include any of the dicyclohexylbenzene isomers and tricyclohexylbenzene isomers described above, and combinations and mixtures of at least two thereof in any proportion.

Described herein is a process for producing phenol by oxidation of oxidation of cyclohexylbenzene to produce an oxidation effluent comprising cyclohexylbenzene hydroperoxide, followed by cleavage of at least a portion of the cyclohexylbenzene hydroperoxide in the presence of a solid acid catalyst, such as an acidic molecular sieve. In the present process, at least a portion of the oxidation effluent is subjected to a concentrating step such that the feed to the cleavage reaction has a higher concentration of cyclohexylbenzene hydroperoxide than the oxidation effluent. Surprisingly, it has now been found that such concentration of the cyclohexylbenzene hydroperoxide in the cleavage feed increases the cycle life of the solid acid cleavage catalyst.

In one preferred embodiment, the present cleavage process forms part of an integrated process for producing phenol and cyclohexanone from benzene, in which benzene is converted to cyclohexylbenzene, which is then oxidized to cyclohexylbenzene hydroperoxide, which, in turn, is cleaved to produce phenol and cyclohexanone. The present process will therefore now be more particularly described with reference to this preferred embodiment.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following reaction:

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), and MCM-56 (described in U.S. Pat. No. 5,362,697). Other molecular sieves, such as UZM-8 (described in U.S. Pat. No. 6,756,030), may be used alone or together with a MCM-22 molecular sieve. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. In one embodiment, where the MCM-22 family molecular sieve is an aluminosilicate, the amount of hydrogenation metal present is such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. However, in a more preferred embodiment, at least 50 wt %, for example at least 75 wt %, and generally substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Georgia and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100 to about 300° C., a pressure of about 800 kPa to about 3500 kPa, a weight hourly space velocity of about 1 to about 10 hf$^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminophosphate, amorphous silica-alumina, an acidic clay, a mixed metal oxide, such as WO$_x$/ZrO$_2$, phosphoric acid, sulfated zirconia and mixtures thereof. Generally, the acid catalyst includes at least one aluminosilicate, aluminophosphate or silicoaluminophosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically is from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only part of the benzene feed but also part of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 14.5 psig to 500 psig (100 kPa to 3550 kPa), a weight hourly space velocity of about 0.2 to 50 hf$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene, and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to the corresponding hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air or other conventional means.

The oxidation is conducted in the presence of a catalyst. Suitable oxidation catalysts include N-hydroxy substituted cyclic imides described in U.S. Pat. No. 6,720,462, which is incorporated herein by reference for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy(pyromellitic diimide), N,N'-dihydroxy(benzophenone-3,3',4,4'-tetracarboxylic diimide), N-hydroxymaleimide, pyridine-2,3-dicarboximide, N-hydroxysuccinimide, N-hydroxy(tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt or N-hydroxy-o-benzenedisulphonimide may be used. Preferably, the catalyst is N-hydroxyphthalimide. Another suitable catalyst is N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Typically, the N-hydroxy substituted cyclic imide or the N,N',N"-trihydroxyisocyanuric acid is employed in an amount between 0.0001 wt % to 15 wt %, such as between 0.001 to 5 wt %, of the cyclohexylbenzene.

Suitable conditions for the oxidation step include a temperature between about 70° C. and about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to cyclohexylbenzene, and may further efficaciously provide contacting of oxygen and cyclohexylbenzene to effect the oxidation reaction. For example, the oxidation reactor may comprise a simple, largely open vessel with a distributor inlet for the oxygen-containing gas stream. In various embodiments, the oxidation reactor may have means to withdraw and pump a portion of its contents through a suitable cooling device and return the cooled portion to the reactor, thereby managing the heat generated in the oxidation reaction. Alternatively, cooling coils providing indirect cooling, say by cooling water, may be operated within the oxidation reactor to remove the generated heat. In other embodiments, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Typically, the product of the cyclohexylbenzene oxidation reaction contains at least 5 wt %, such as at least 10 wt %, for example at least 15 wt %, or at least 20 wt % cyclohexyl-1-phenyl-1-hydroperoxide based upon the total weight of the oxidation reaction effluent. Generally, the oxidation reaction effluent contains no greater than 80 wt %, such as no greater than 60 wt %, or no greater than 40 wt %, or no greater than 30 wt %, or no greater than 25 wt %, of cyclohexyl-1-phenyl-1-hydroperoxide based upon the total weight of the oxidation reaction effluent. The oxidation reaction effluent may further comprise imide catalyst and residual cyclohexylbenzene. For example, the oxidation reaction effluent may include residual cyclohexylbenzene in an amount of at least 50 wt %, such as at least 60 wt %, or at least 65 wt %, or at least 70 wt %, or at least 80 wt %, or at least 90 wt %, based upon total weight of the oxidation reaction effluent.

Before being supplied to the downstream cleavage reaction, in the present process at least a portion of the oxidation reaction effluent is subjected to a concentrating step so that the feed to the cleavage reaction has a higher concentration of cyclohexylbenzene hydroperoxide than the oxidation effluent. For example, the concentrating step may increase the concentration of cyclohexylbenzene hydroperoxide in the cleavage feed by at least 10 wt %, such as at least 20 wt %, as compared with the oxidation effluent. Desirably, the concentrating step comprises subjecting all or a fraction of the oxidation reaction effluent to high vacuum distillation to generate a product enriched in cyclohexylbenzene and leave a material which is concentrated in the desired cyclohexyl-1-phenyl-1-hydroperoxide. This material may then be used as the feed to the cleavage reaction. In one embodiment, the cleavage feed comprises from 30 wt % to 80 wt % by weight, such as from 35 wt % to 70 wt %, or from 40 wt % to 60 wt %, or from 40 wt % to 50 wt %, of cyclohexylbenzene hydroperoxide. In an advantageous embodiment, in the concentrating step, the oxidation reaction effluent is partly evaporated under a high vacuum of at most 2.70 kPa generated by using a liquid seal vacuum pump to form (a) a liquid/vapor mixture rich in cyclohexylbenzene, which is then condensed to obtain a cyclohexylbenzene-rich stream, which is removed and/or recycled to cyclohexylbenzene oxidation step, and (b) a liquid stream having a higher cyclohexylbenzene hydroperoxide concentration than the oxidation reaction effluent. In another embodiment, the oxidation reaction effluent may be cooled to a temperature sufficient low such that the cyclohexylbenzene hydroperoxide precipitates as crystals, which are then separated and collected as high-concentration cyclohexylbenzene hydroperoxide for use in the cleavage step.

Additionally, all or a fraction of the oxidation effluent, or all or a fraction of the material left after vacuum distillation, may be cooled to cause crystallization of the residual imide oxidation catalyst, which can then be separated either by filtration or by scraping from a heat exchanger surface used to effect the crystallization. At least a portion of the resultant cyclohexylbenzene hydroperoxide material may be subjected to the cleavage reaction.

As another example, all or a fraction of the oxidation effluent, or all or a fraction of the material left after vacuum distillation, may be subjected to water washing and then passage through an adsorbent, such as a molecular sieve, to separate the imide oxidation catalyst (e.g., NHPI) and other adsorbable compounds, and provide a material for the cleavage reaction. Similarly, all or a fraction of the oxidation effluent, or all or a fraction of the material left after vacuum distillation, may undergo a chemically or physically based adsorption, such as passage over a bed of sodium carbonate to remove the imide oxidation catalyst and other adsorbable components, before being subjected to the cleavage reaction. Another possible separation involves contacting all or a fraction of the oxidation effluent, or all or a fraction of the material left after vacuum distillation, with a liquid containing a base, such as an aqueous solution of an alkali metal carbonate or bicarbonate, before being subjected to the cleavage reaction. An example of separation by basic material treatment is disclosed in International Application No. WO 2009/025939, the entire contents of which are incorporated herein by reference.

In another embodiment, all or a fraction of the oxidation effluent, or all or a fraction of the material left after vacuum distillation, may be contacted with an aluminosilicate zeolite of the FAU type to reduce the amount of residual imide catalyst in the effluent by adsorption onto the zeolite. The FAU type zeolite employed to remove the oxidation catalyst may have a unit cell size less than 24.35 Å, such as less than 24.30 Å, and the contacting to remove the oxidation catalyst can be conducted prior to or concurrently with the cleavage reaction. The FAU type zeolite employed to remove the oxidation catalyst may be the same or different from the one used in the cleavage reaction according to the present disclosure. The adsorbed imide catalyst can be desorbed from the FAU type zeolite by washing with a polar solvent, such as acetone or cyclohexanone, and recovered by flashing off the solvent and/or by recrystallization. The recovered imide can then be recycled to the oxidation reaction.

Hydroperoxide Cleavage

After the concentrating step and any other optional treatment to remove residual imide catalyst, the cleavage feed is supplied to one or more cleavage reaction zones where at least a portion of the cyclohexyl-1-phenyl-1-hydroperoxide in the feed undergoes acid-catalyzed cleavage to produce phenol and cyclohexanone.

The acid catalyst used in the present cleavage reaction comprises a solid acid, such an acidic molecular sieve, for example an aluminosilicate zeolite. Examples of suitable acidic molecular sieves include at least one of zeolite beta, faujasite, ZSM-12, mordenite and an MCM-22 family molecular sieve. In one embodiment, the cleavage catalyst comprises a FAU-type zeolite having a unit cell size less than 24.50 Angstroms ("Å"), such as less than or equal to 24.45 Å, or less than or equal to 24.40 Å, or less than or equal to 24.35 Å, or less than or equal to 24.30 Å, or even less than or equal to 24.25 Å. Unit cell size is determined by X-ray diffraction as described in ASTM D-3942. As used herein, the terms "faujasite," "FAU-type zeolite" and "zeolite of the FAU type" are used interchangeably to mean a zeolite having a FAU-type structure as described in the *Atlas of Zeolite Framework Types*, Ch. Baerlocher et al. (6th Ed. 2007). The zeolite can be used in unbound form or can be combined with a binder, such as silica or alumina, such that the overall catalyst (zeolite plus binder) comprises from about 5 wt % to about 95 wt % of the final catalyst material.

In embodiments, the cleavage catalyst has a pore volume as measured by nitrogen ($N_2$) adsorption of greater than 0.3 $cm^3/g$, or greater than 0.4 $cm^3/g$, or greater than 0.5 $cm^3/g$. In embodiments, the cleavage catalyst contains less than 6 wt %, or less than 3 wt %, or less than 1 wt %, or less than 0.5 wt % of Group 3 to Group 12 metals including the lanthanide series, based upon the weight of the catalyst.

In embodiments, the cleavage reaction is conducted under conditions including a temperature in a range from 20° C. to 200° C., such as from 40° C. to 120° C. and an absolute pressure of about 100 kPa to 2000 kPa, such as 100 kPa to 1000 kPa, such that the cleavage reaction mixture is completely or predominantly in the liquid phase during the cleavage reaction. The weight hourly space velocity may be in a range from 1 to 1000 $hour^{-1}$ on total feed, such as from 1 to 500 $hour^{-1}$, or from 1 to 300 $hour^{-1}$.

The cleavage reaction can be conducted in a variety of reactor configurations and in either a single reactor or in a plurality of reactors. For example, the reaction may be conducted at least in a first reactor and a second reactor connected in series, with the first reactor being operated at a temperature from 20° C. to 120° C. and an absolute pressure from 100 kPa to 500 kPa and the second reactor being operated at a temperature from 30° C. to 180° C. and an absolute pressure of about 100 kPa to about 1000 kPa. The first and second reactors may be the same or different and may also be connected in parallel such that neither receive as its feed an effluent from the other reactor.

In one embodiment, the cleavage reaction is conducted in a slurry reactor, in a configuration such as a stirred tank, or a pump-around loop. In another embodiment, at least a portion of the cleavage reaction is conducted in a continuous stirred tank reactor (CSTR), with the catalyst being slurried in the cleavage reaction medium. In embodiments, the catalyst is used in an amount from 50 ppm to 10 wt % of the cleavage reaction medium processed per hour. Advantages for this configuration include easy heat management and flexibility to add/withdraw catalyst to maintain conversion as the catalyst deactivates over time. Catalyst deactivated over time can be also regenerated by burning off coke in air. In case the catalyst is also used for recovery of the imide catalyst, this air-regeneration is advantageously performed after recovering the adsorbed catalyst by washing using a solvent. In a slurry cleavage process, the catalyst can be regenerated on various schedules. Advantageously, the catalyst can be continuously withdrawn from the cleavage reactor, regenerated in an external recycle loop, and then returned into the cleavage reactor. Under such an operation regime, a steady state of catalyst activity can be maintained through regeneration and by continuously replacing a fraction of the recycled catalyst with fresh catalyst.

The solid acid catalyst can also be used in a fixed bed plug-flow reactor with or without first removing the imide catalyst from the cleavage feed stream. If the imide catalyst is not removed, the catalyst bed may adsorb it, allowing its recovery and recycle to the oxidation process. In such a process design, two or more parallel cleavage reactor trains may be employed to enable uninterrupted processing of the peroxide feed. Thus, as the catalyst is saturated with the imide catalyst causing it to deactivate in one reactor train, the cleavage feed can be switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction using the solid acid catalyst may have a cyclohexylbenzene hydroperoxide conversion of greater than 30%, or greater than 50%, or greater than 70%, or greater than 90%, or greater than 95%, or greater than 99%, or even 100%. The phenol selectivity may be greater than 60%, or greater than 70%, or greater than 90%, or greater than 95%. The cyclohexanone selectivity may be greater than 27%, or greater than 50%, or greater than 70%, or greater than 80%, or greater than 85%, or greater than 90%. As used herein, "cyclohexylbenzene hydroperoxide conversion" means the percentage of cyclohexylbenzene hydroperoxide converted to any product, including but not limited to phenol and cyclohexanone. Phenol selectivity (Sp) and cyclohexanone selectivity (Sc) are calculated as follows:

$$Sp = \frac{\text{Amount of phenol produced (mole)}}{\text{Amount of cyclohexybenzene hydroperoxide converted (mole)}} \times 100\%$$

$$Sc = \frac{\text{Amount of cyclohexanone produced (mole)}}{\text{Amount of cyclohexylbenzene hydroperoxide converted (mole)}} \times 100\%$$

The major products of the cleavage reaction are phenol and cyclohexanone, each of which generally constitutes about 40 wt % to about 60 wt %, or about 45 wt % to about 55 wt % of the cleavage effluent, based on the weight of the conversion products of the cleavage reaction.

The cleavage effluent is removed from the cleavage reaction zone and can be divided into at least a cleavage product stream, from which phenol and/or cyclohexanone can be recovered, and a cleavage recycle stream, which is returned to the cleavage reaction zone to form a portion of a cleavage reaction mixture with the cyclohexylbenzene hydroperoxide from the oxidation step. The recycle stream can be used to control exothermic heat rise in the cleavage reaction zone and, in one embodiment, the weight ratio of the cleavage recycle stream to the cleavage product stream ranges from 1 to 50, such as from 1 to 40, from 1 to 30, from 2 to 20, from 2 to 15, or from 2 to 10. Division of the cleavage effluent into at least the cleavage product stream and the cleavage recycle stream may or may not involve a fractionation step to reduce the level of one or more of components in the recycle stream (such as, phenol, cyclohexanone and/or cyclohexylbenzene) as compared with the cleavage effluent.

In some embodiments, it may be desirable to supply a polar solvent to the cleavage reaction zone along with the cyclohexylbenzene hydroperoxide from the oxidation step and the cleavage recycle stream. The polar solvent may be added to the cleavage reaction zone as a separate stream, together with the cyclohexylbenzene hydroperoxide-containing stream from the oxidation step as a combined stream or, desirably, together with the cleavage recycle stream in a combined stream. This is because, due to the high phenol concentration in the recycle stream, the recycle stream tends to have a higher polarity than the fresh cyclohexylbenzene hydroperoxide stream and would mix better with the polar solvent. Suitable polar solvents include alcohols containing less than 6 carbons, such as ethanol, methanol, phenol, propanol, isopropanol and butanols. However, many of these organic solvents may react with cyclohexanone and thus influence product yield and purity. Thus, the preferred polar solvent is water. Although the mechanism is not fully understood, the polar solvent is found to decrease the deactivation rate of the solid acid catalyst used in the cleavage reaction.

In one embodiment, the polar solvent is added to the cleavage reaction zone in an amount from 100 ppm to 10 wt %, such as from 1000 ppm to 5 wt %, or 2000 ppm to 4 wt % of the cleavage reaction mixture. In some embodiments, the cleavage reaction mixture also contains from 5 wt % to 50 wt % phenol, from 5 wt % to 50 wt % cyclohexanone, from 1 wt % to 10 wt % cyclohexylbenzene hydroperoxide, and from 5 wt % to 60 wt % cyclohexylbenzene. In other embodiments, the cleavage reaction mixture also contains from 20 wt % to 40 wt % phenol, from 20 wt % to 40 wt % cyclohexanone, no greater than 6 wt % cyclohexylbenzene hydroperoxide, and from 15 wt % to 40 wt % cyclohexylbenzene.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam and nylons, such as nylon 6 and nylon 6,6.

The phenol produced through the processes disclosed herein may be used, for example, to produce phenolic resins, bisphenol A, ϵ-caprolactam, adipic acid, and/or plasticizers.

The invention will now be more particularly described with reference to the following non-limiting Examples.

EXAMPLES

In a series of three tests, a fresh fixed bed of faujasite catalyst, was used in a cleavage reactor with the ability to recycle the product.

Test A, in Recycle Mode

In this test, an oxidation product mixture comprising 20 wt % to 25 wt % of cyclohexylbenzene hydroperoxide and the balance primarily cyclohexylbenzene was diluted with equal amounts of phenol and cyclohexanone. The resultant material was then fed to the cleavage reactor on a once-through basis, i.e., with no recycle of the products, so as to simulate the feed the catalyst would be exposed to if the reactor were operating with the oxidation product mixture as feed and a 5:1 product/feed recycle ratio (i.e., a feed comprising about 5 wt % cyclohexylbenzene hydroperoxide, about 10 wt % phenol, about 10 wt % cyclohexanone, and balance cyclohexylbenzene). In an operation in this test, the oxidation product mixture, which corresponds to the cleavage feed in the process of the present disclosure, would have a cyclohexylbenzene hydroperoxide concentration in a range from 20 wt % to 25 wt %.

Test B, without Product Recycle

In this test, an oxidation product mixture comprising 20-25 wt % of cyclohexylbenzene hydroperoxide and the balance primarily cyclohexylbenzene was diluted with cyclohexylbenzene. The resultant material, comprising about 5 wt % cyclohexylbenzene hydroperoxide and balance cyclohexylbenzene, was then fed to the cleavage reactor on a once-through basis, i.e., with no recycle of the products, so as to simulate the feed the catalyst would be exposed to if the reactor were operating with a non-concentrated oxidation product mixture as feed (i.e., a feed comprising about 5% cyclohexylbenzene hydroperoxide, and balance cyclohexylbenzene). In an operation in this test, the oxidation product mixture after dilution with cyclohexylbenzene, which corresponds to the cleavage feed in the process of the present disclosure, would have a cyclohexylbenzene hydroperoxide concentration of about 5 wt %.

Figure 1:
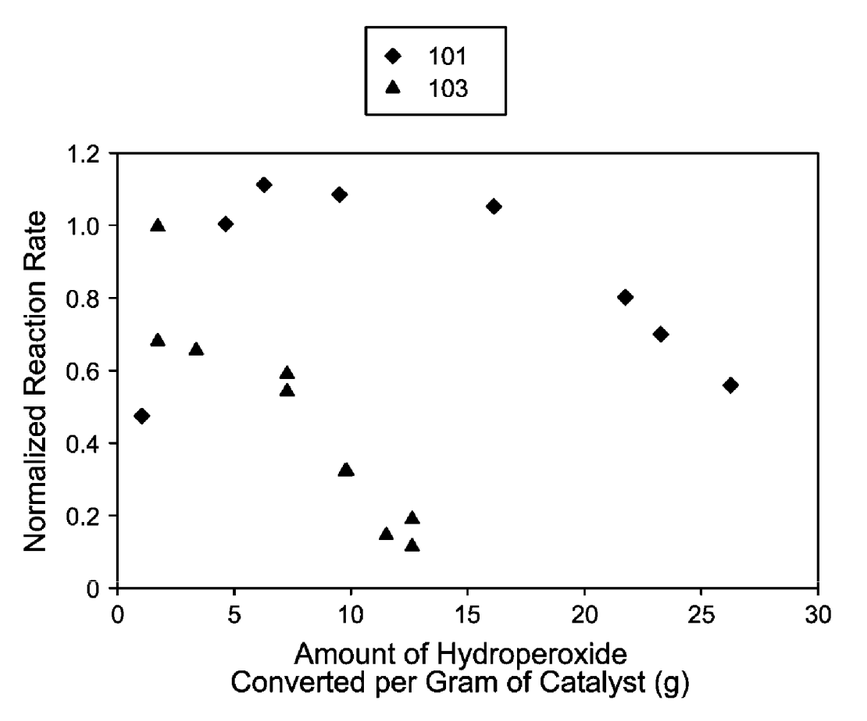
FIG. 1 is a graph of the normalized reaction rate (rate normalized to initial rate) as a function of the amount of cyclohexylbenzene hydroperoxide processed per gram of faujasite catalyst for the cyclohexylbenzene hydroperoxide cleavage tests described in Tests A and B in the Example.

The calculated rates in each experiment were then normalized with respect to the initial rate in that experiment and plotted as a function of the amount of cyclohexylbenzene hydroperoxide converted per gram of catalyst, shown in FIG. 1. Data series 101 correspond to Test A, and data series 103 to Test B. As this diagram clearly shows, in Test A, the life of the catalyst was much longer than in Test B. This demonstrates the benefit of concentrating the cyclohexylbenzene oxidation product before feeding to the cleavage reactor.

While the present invention has been described and illustrated by reference to particular embodiments, those of ordinary skill in the art will appreciate that the invention lends itself to variations not necessarily illustrated herein. For this reason then, reference should be made solely to the appended claims for purposes of determining the true scope of the present invention.

The invention claimed is:

1. A process for producing phenol, the process comprising:
   (a) contacting cyclohexylbenzene with an oxygen-containing gas in the presence of an oxidation catalyst under oxidation conditions effective to produce an oxidation effluent comprising cyclohexylbenzene hydroperoxide at a first concentration Con1 and residual cyclohexylbenzene;
   (b) concentrating at least a portion of the oxidation effluent to produce a cleavage feed comprising cyclohexylbenzene hydroperoxide at a second concentration Con2, where Con2>Con1; and
   (c) contacting a cleavage reaction mixture formed from the cleavage feed with a solid acid catalyst in a cleavage reaction zone under conditions effective to produce a cleavage product comprising phenol and cyclohexanone;
   (d) dividing the cleavage product into a first fraction and a second fraction, each comprising phenol and cyclohexanone;
   (e) supplying a polar solvent comprising water to the second fraction to form a combined recycle stream; and
   (f) providing the combined recycle stream to the cleavage reaction zone.

2. The process of claim 1, wherein the concentrating step (b) comprises distillation to remove at least a portion of the cyclohexylbenzene in the oxidation effluent.

3. The process of claim 1, wherein Con2−Con1>10 wt %.

4. The process of claim 1, wherein Con2−Con1>20 wt %.

5. The process of claim 1, wherein Con1 is in a range from 10 wt % to 30 wt % and Con2 is in a range from 30 wt % to 80 wt %.

6. The process of claim 1, wherein Con1 is in a range from 15 wt % to 25 wt % and Con2 is in a range from 40 wt % to 60 wt %.

7. The process of claim 1, wherein the weight ratio of the first fraction to the second fraction is in a range from 1 to 50.

8. The process of claim 1, wherein the solid acid catalyst comprises an acidic molecular sieve.

9. The process of claim 8, wherein the acidic molecular sieve comprises an aluminosilicate zeolite.

10. The process of claim 8, wherein the acidic molecular sieve comprises at least one of zeolite beta, faujasite, ZSM-12, mordenite and an MCM-22 family molecular sieve.

11. The process of claim 1, further comprising:
    (g) regenerating at least a portion of the solid acid catalyst.

12. A process for producing phenol, the process comprising:
    (a) hydroalkylating benzene with hydrogen in the presence of a hydroalkylation catalyst under conditions effective to produce a hydroalkylation reaction product comprising cyclohexylbenzene;
    (b) contacting at least a portion of the cyclohexylbenzene from the hydroalkylation reaction product with an oxygen-containing gas in the presence of an oxidation catalyst under oxidation conditions effective to produce an oxidation effluent comprising cyclohexylbenzene hydroperoxide at a first concentration Con1 and residual cyclohexylbenzene;
    (c) concentrating at least a portion of the oxidation effluent to produce a cleavage feed comprising cyclohexylbenzene hydroperoxide at a second concentration Con2, where Con2>Con1; and
    (d) contacting a cleavage reaction mixture formed from the cleavage feed with a solid acid catalyst in a cleavage reaction zone under conditions effective to produce a cleavage product comprising phenol and cyclohexanone;
    (e) dividing the cleavage product into a first fraction and a second fraction, each comprising phenol and cyclohexanone;
    (f) supplying a polar solvent comprising water to the second fraction to form a combined recycle stream; and
    (g) providing the combined recycle stream to the cleavage reaction zone.

13. The process of claim 12, wherein the concentrating step (b) comprises distillation to remove at least a portion of the residual cyclohexylbenzene in the oxidation effluent.

14. The process of claim 12, wherein Con2−Con1>10 wt %.

15. The process of claim 12, wherein Con2−Con1>20 wt %.

16. The process of claim 12, wherein Con1 is in a range from 10 wt % to 30 wt %, and Con2 is in a range from 30 wt % to 80 wt %.

17. The process of claim 12, wherein Con1 is in a range from 15 wt % to 25 wt %, and Con2 is in a range from 40 wt % to 60 wt %.

18. The process of claim 12, wherein the weight ratio of the first fraction to the second fraction is from 1 to 50.

19. The process of claim 12, wherein the solid acid catalyst comprises an acidic molecular sieve.

20. The process of claim 19, wherein the acidic molecular sieve comprises an aluminosilicate zeolite.

21. The process of claim 19, wherein the acidic molecular sieve comprises at least one of zeolite beta, faujasite, ZSM-12, mordenite and an MCM-22 family molecular sieve.

22. The process of claim 12, further comprising:
(e) regenerating at least a portion of the solid acid catalyst.

* * * * *